United States Patent [19]
Rich et al.

[11] Patent Number: 4,865,038
[45] Date of Patent: Sep. 12, 1989

[54] SENSOR APPLIANCE FOR NON-INVASIVE MONITORING

[75] Inventors: David Rich, E. Hartford, Conn.; Simon Thomas, Whitland, Wales

[73] Assignee: Novametrix Medical Systems, Inc., Wallingford, Conn.

[21] Appl. No.: 916,938

[22] Filed: Oct. 9, 1986

[51] Int. Cl.$^4$ .............................................. A61B 5/00
[52] U.S. Cl. ................................... 128/633; 128/664; 128/665; 356/41
[58] Field of Search ............. 128/644, 666, 696, 633, 128/639, 664, 665, 690, 798, 802; 356/41; 250/551

[56] References Cited

U.S. PATENT DOCUMENTS

| | | | |
|---|---|---|---|
| 4,091,803 | 5/1978 | Pinder | 128/690 |
| 4,129,124 | 12/1978 | Thalmann | 128/690 |
| 4,160,308 | 7/1979 | Courtney et al. | 250/551 |
| 4,213,463 | 7/1980 | Osenkarski | 128/639 |
| 4,233,987 | 11/1980 | Feingold | 128/639 |
| 4,380,240 | 4/1983 | Jobsis et al. | 128/633 |
| 4,635,641 | 1/1987 | Hoffman | 128/639 |
| 4,636,647 | 1/1987 | Nishizawa | 250/551 |
| 4,700,708 | 10/1987 | New, Jr. et al. | 128/633 |
| 4,726,382 | 2/1988 | Boehmer et al. | 128/667 |

Primary Examiner—Ruth S. Smith
Attorney, Agent, or Firm—Howard F. Mandelbaum

[57] ABSTRACT

A sensor appliance removably attachable to a living body for non-invasively producing signals indicative of a condition of the body and applying them to a monitoring or measuring device and method of making the appliance characterized by a small, highly flexible light weight substrate with surface mounted light emitting and photodetector components hermetically sealed in a flexible moisture resistant envelope. Provision is made for inclusion of a form sustaining spine to enhance positional stability.

17 Claims, 2 Drawing Sheets

FIG. 1
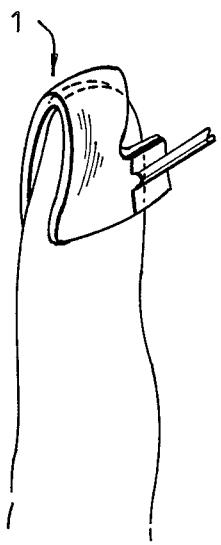
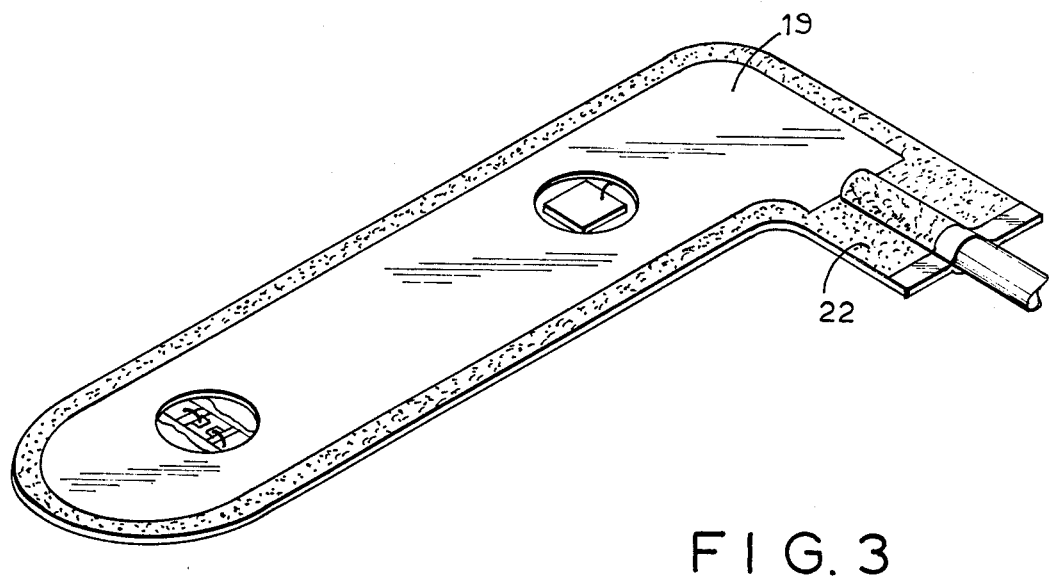
FIG. 3

20

SENSOR APPLIANCE FOR NON-INVASIVE MONITORING

BACKGROUND OF THE INVENTION

This invention is related to the use of sensors applied to the body for monitoring or making measurements of body tissue condition, metabolism or other body functions indicative of health. More specifically, the invention is directed to an appliance which can be readily attached to the body to support a sensor adjacent thereto in a stable disposition for accurate and precise measurements unhampered by artifact due to sensor motion relative to the body.

One application for a sensor appliance of the type described herein is in pulse oximetry, a non-invasive method of measuring the relative oxygen saturation of the blood. Pulse oximeters generally employ light sources, e.g., light emitting diodes (L.E.D.s), to alternately direct light of two different wave lengths, e.g., red and infra-red, to the blood through the skin. The light transmitted or reflected by the blood at the different wave lengths can then be compared to provide a measurement of oxygen saturation.

Typically, a sensor appliance containing the light sources, e.g., L.E.D.s, and a light sensor, e.g., photodetector, is mounted on the finger, toe or ear lobe. An example of such a sensor is disclosed in European patent application No. 84302994.3 for a Sensor having Cutaneous Conformance. In prior art sensor appliances, individual L.E.D.s and a photodetector of an oximeter sensor are each mounted on a respective rigid substrate which is, in turn, incorporated into a flexible envelope, making for a bulky device which often result in unstable readings due to limited conformability when attached to a patient. In addition to yielding unstable readings due to limited conformability, prior art appliances are subject to contamination and suitable for use only as disposable devices since their discrete LED and photodiode components and wiring are relatively bulky and vulnerable to external contaminants. Moreover, such appliances cannot be readily cleaned for use on multiple patients. Flexibility in the areas of the light sources and detectors is minimal thereby preventing good conformance with small toes, fingers and earlobes as in the case of neonates. In addition, disassembly of and/or damage to the structure of prior art appliances often results from attempts at repeated usage.

SUMMARY OF THE INVENTION

The foregoing problems and others associated with prior art sensor appliances are overcome by the instant invention which provides for a sensor appliance adapted for removable attachment to a living body for non-invasively producing signals indicative of a condition of the body and applying them to a monitoring or measuring device, including an elongated flexible substrate disposed within an outer flexible sealed envelope and having energy transmitting means and sensor means integrally bonded therewith and signal conductor means operatively connected to said sensor means for connection to a monitoring or measuring device, and rigid support means bonded to an opposite side of said substrate adjacent the sensor means for enhancing wire bonding and preventing delamination of the encapsulating epoxy of the appliance structure during flexing thereof.

It is therefore an object of the invention to provide a sensor appliance adapted for removable attachment to a living body for non-invasively producing signals indicative of a condition of the body.

Another object of the invention to provide a sensor appliance suitable for repeated use among several patients.

Still another object of the invention to provide a sensor appliance which is conformable to the surface of the body at which it is positioned thereby resisting motion with respect to the body.

A further object of the invention to provide a sensor appliance which can be readily disinfected between uses.

Still a further object of the invention to provide a sensor appliance having a very low profile for enhanced flexibility.

An additional object of the invention to provide a sensor appliance which is hermetically sealed so that its active components are impervious to contamination.

Other and further objects of the invention will be apparent from the following drawings and description of a preferred embodiment of the invention in which like reference numerals are used to indicate like parts in the various views.

DESCRIPTION OF THE DRAWINGS

FIG. 1 is an environmental view of the preferred embodiment of the invention in its intended use.

FIG. 3 is a perspective view of the preferred embodiment of the invention.

DESCRIPTION OF THE PREFERRED EMBODIMENT

Figure 2:
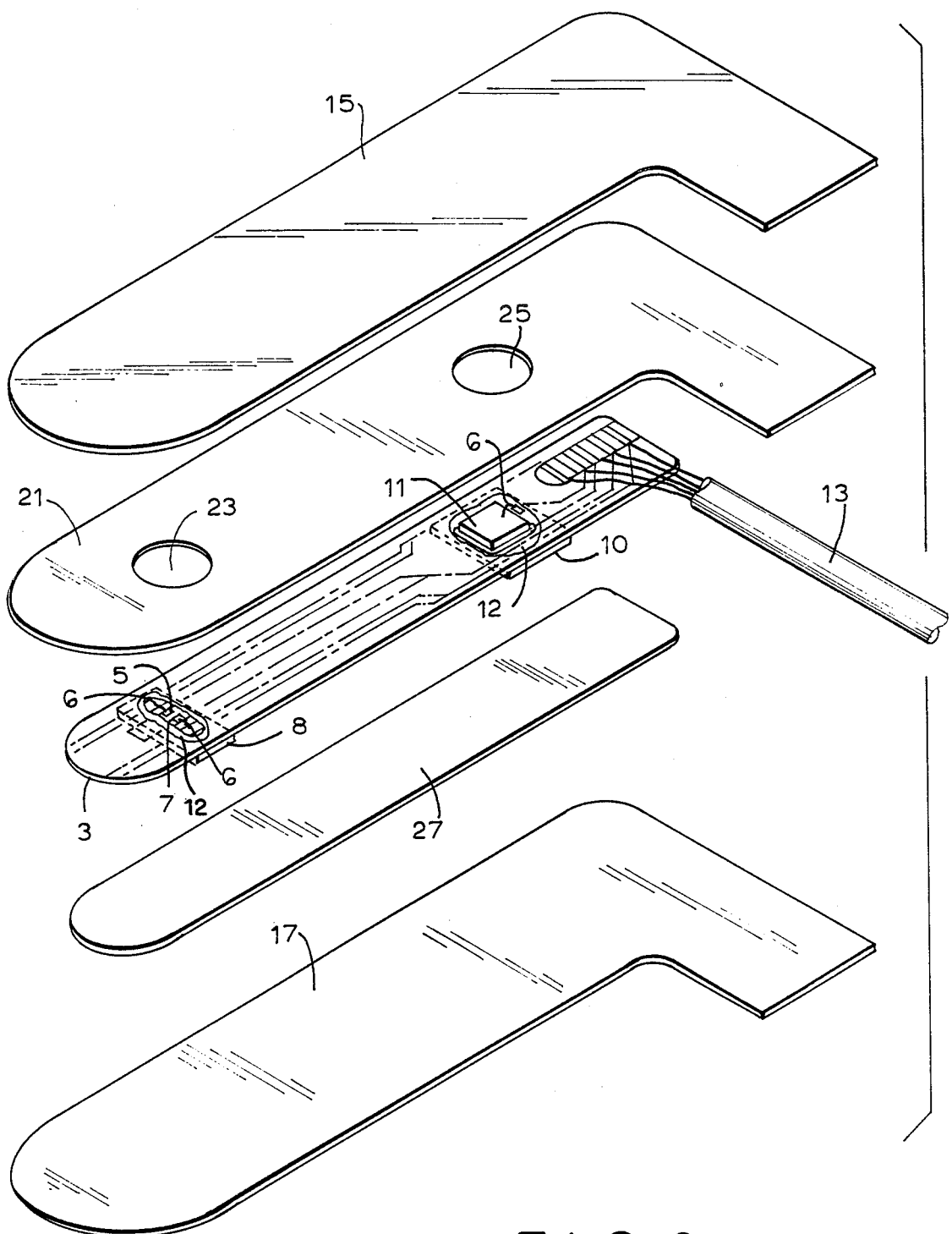
FIG. 2 is an exploded perspective view of the preferred embodiment of the invention.

Referring now to FIG. 1 of the drawings, there is shown a sensor appliance 1, in accordance with the invention, disposed on the finger of a patient. The sensor appliance 1, as shown, is used in oximetry, i.e., the measurement of percent oxygen saturation of the blood. However, it is to be appreciated that the structure disclosed herein may have application in other measurements or monitoring of body condition, function or metabolism where it is desired to mount a sensor on the body of a patient.

Referring now to FIGS. 2 and 3 of the drawings, there is shown an elongated flexible printed circuit board substrate 3 having a very low profile, i.e., a thickness of approximately 0.15 millimeters. The flexible substrate 3 is preferably formed from a strong, light weight material suitable for component surface mounting and wire bonding.

Two die light emitting diodes 5 and 7 are respectively bonded to the flexible printed circuit board substrate 3 by a suitable bonding agent which, in the case of the preferred embodiment of the invention is a die attachment epoxy that forms a first bond to the flexible printed circuit board substrate 3. The die attachment epoxy is selected to have high thermal conductivity thereby serving as a heat sink and dissipating the heat generated by the LEDs 5 and 7 when they are energized. The die attachment epoxy is also selected to have high electrical conductivity. A second contact to the L.E.D. dice is made by means of wire bonds 6 between the die contact pads and appropriate adjacent tracks formed by conductors 9 on the printed circuit board.

As is known in oximetry, the transmission of light in the red range of the spectrum, i.e., at a wave length of approximately 660 nanometers through blood is substantially affected by the amount of oxygenated hemoglobin present in the blood. The transmission of light in the infra-red range of the spectrum, i.e., at a wave length of approximately 940 nanometers through blood is substantially unaffected by the amount of oxygenated hemoglobin present in the blood. Oximeters use this principal to alternately illuminate the blood through the skin tissue with light of the foregoing respective wave lengths. Hence, in accordance with the present invention, the LED 5 emits light in the red range at 660 nm and the LED 7 emits light in the infra-red range at approximately 940 nm. The die LEDs 5 and 7 include no separate wire leads or package as found in conventional LEDs but only the light emitting elements which are die attached and wire bonded directly to suitably plated copper conductors 9 on the surface of the flexible printed circuit board substrate 3 through which the die LEDs 5 and 7 are alternately energized. In the preferred embodiment of the invention, the copper conductors 9 are plated with 0.99999 pure neutral gold. Other materials having similar conductivity may be employed. The substrate 3 can be in the form of a flexible circuit such as a commercially available Kapton flex circuit.

Also mounted on the flexible printed circuit board substrate 3 at its opposite end is a die photodetector 11 which is directly die attached and wire bonded to other copper conductors 9 for transmitting signals produced by the die photodetector 11 to an oximeter or other monitor (not shown) through a cable 13. Like the die LEDs 5 and 7, the die photodetector 11 includes no separate wire leads or package as found in conventional photodetectors but only the light detecting element, the two contacts of which are die attachment epoxy and wire bonded, respectively, directly to suitably plated copper conductors 9 on the surface of the flexible printed circuit board substrate 3 through which the output signals produced by the die photodetector 11 are transmitted to the oximeter or monitor.

The die LED 5 and 7, and the die photodetector 11 are covered with an encapsulating mound 12 formed from a glob-top epoxy, that is, a high viscosity epoxy which does not flow beyond the area to which it is applied and hardens into a bead having a substantially smooth and spherical exposed surface, which is transparent to light having a wave length in the range of 660 nanometers to 940 nanometers. The glob-top epoxy mound 12 forms a rigid protective shield which helps stabilize the die LED 5 and 7, and die photodetector 11 relative to the flexible printed circuit board substrate 3 and which absorbs any external impact which may be applied to the die LED 5 and 7 and die photodetector 11.

Bonded to the underside of the substrate 3, immediately beneath the LEDs 5 and 7, and die photodetector 11 are rigid supports 8 and 10. The supports 8 and 10 are preferably made of a light weight rigid material, e.g., a rigid plastic or reinforced epoxy to provide local support only in the areas of the LEDs 5 and 7, an die photodetector 11 to facilitate die attachment and wire bonding without significantly compromising the flexibility of the substrate 3 and appliance 1 as a whole.

The flexible printed circuit board substrate 3 with the die LEDs 5 and 7, die photodetector 11, and suitably plated copper conductors 9 mounted on it is sandwiched between the upper and lower layers 15 and 17, respectively of a vinyl envelope 19. The lower layer 17 is preferably formed from a sheet of highly flexible white opaque vinyl or similar material. The upper layer 15 is preferably formed from a sheet of highly flexible transparent vinyl or similar material to enable light to be transmitted from the die LEDs 5, 7, through the upper envelope layer 15, and after passing through the body tissue, again through the upper envelope layer 15, to the die photodetector 11.

Disposed between the upper envelope layer 15 and lower envelope layer 17 is a spacer 21 formed from a sheet of highly flexible white opaque vinyl or similar material of dimensions similar to the like dimensions of the upper envelope layer 15 and lower envelope layer 17. The spacer 21 is provided with circular apertures 23 and 25 which are positioned in alignment with the die LEDs 5 and 7 and the die photodetector 11, respectively, as shown in FIG. 3. Polyvinylchloride (PVC) has been found to be a suitable material for the envelope 19 and spacer 21.

A supporting spine member 27 may be disposed within the envelope 19 between the flexible printed circuit board substrate 3 and the lower envelope layer 17. The spine member 27 is preferably formed from a malleable form sustaining material such as a thin sheet of metal. In the preferred embodiment of the invention, an aluminum spine having a shape congruent to that of the flexible printed circuit board substrate 3 is employed.

Presence of the spine 27 permits the sensor appliance 1 to be held in place on the body member, e.g., finger, simply by bending and pressing the spine member 27 about the member into a snug fit. The form sustaining property of the spine 27, thereafter, maintains the sensor appliance 1 in place on the body member. In the absence of the spine member 27, it is necessary to use an adhesive or an external holding or clamping device to maintain the sensor appliance 1 in proper position without movement to enable stable measurement to be accomplished.

The outer edges of the envelope 19, including upper envelope layer 15 and lower envelope layer 17, and spacer 21 are hermetically sealed about their peripheries 22. In the preferred embodiment of the invention the seal is accomplished by RF welding. The envelope 19 is also sealed about the cable 13 so that the flexible printed circuit board substrate 3 is encapsulated in a hermetically impervious environment.

The result is a sensor appliance 1 which can be readily cleaned or disinfected by wiping the surface with alcohol or another suitable sterilizing solution. The structure of the sensor appliance 1 is robust and allows repeated use. Conformability about small body members is enhanced by the low profile and reduced rigidized length of the sensor appliance 1.

When the malleable spine 27 is employed, it enhances ambient light rejection in addition to supporting and maintaining the sensor appliance 1 in place on the body member. Moreover, with the spine member 27 holding the sensor appliance 1 in place, controlled movement of the sensor appliance 1 can be made to obtain the position of most favorable signal response and the position will be maintained with stability after the sensor appliance 1 is released and while an additional adhesive or non-adhesive wrap is applied, if required. The perimeter weld allows for a relatively small sensor appliance 1 since a large surface area is not required to hold the structure together and prevent delamination.

It is to be understood and appreciated that alterations, modifications and variations of and to the preferred embodiment described herein may be made without departing from the spirit and scope of the invention which is defined in the following claims.

What is claimed is:

1. A sensor appliance adapted for removable attachment to a living body for non-invasively producing signals indicative of a condition of the body and applying them to a monitoring or measuring device comprising:

an elongated flexible base comprising a form sustaining material for maintaining the shape of said base when bent about the surface of a body member in conformance therewith for retention thereon, a sensor integrally bonded with a first surface of said base for stable disposition proximate said body member during retention thereon, and a signal conductor connected to said sensor and adapted for connection to said monitoring or measuring device.

2. A sensor appliance according to claim 1 wherein said sensor comprises a die photodetector.

3. A sensor appliance according to claim 2 further comprising an energy source bonded to said base, said sensor producing a signal in response to said energy.

4. A sensor appliance according to claim 3 wherein said sensor is covered with a rigid encapsulating material transparent to the energy emitted by said energy source.

5. A sensor appliance according to claim 4 wherein said rigid encapsulating material comprises a glob-top epoxy.

6. A sensor appliance according to claim 4 wherein said sensor comprises means responsive to light having a wave length in the range of 660 nanometers to 940 nanometers and said transparent rigid encapsulating material comprises a substance transparent to light in said range.

7. A sensor appliance according to claim 1 wherein said base comprises a flexible substrate and a flexible, form sustaining spine comprising said material, and further comprising confining means for holding said substrate and said spine in close proximity.

8. A sensor appliance according to claim 7 wherein said sensor is bonded to said substrate with a thermally conductive surface bonding agent.

9. A sensor appliance according to claim 7 wherein said sensor is bonded to said substrate with an electrically conductive surface bonding agent.

10. A sensor appliance according to claim 9 wherein said surface bonding agent comprises a die attachment epoxy.

11. A sensor appliance according to claim 7 wherein said confining means comprises a flexible sealed envelope.

12. A sensor appliance according to claim 1 further comprising a rigid support mounted on a second surface of said base opposite said sensor.

13. A sensor appliance adapted for removable attachment to a living body for non-invasively producing signals indicative of body tissue content and applying them to a monitor or other measuring device comprising an elongated flexible substrate adapted to be bent about the surface of a body member for conformance therewith and retention thereon, a source of energy integrally bonded with a first area on a first surface of said substrate for transmitting energy to the proximate body tissue, a sensor integrally bonded with a second area on said first surface of said substrate for stable disposition proximate said body member during retention thereon while receiving said energy transmitted by said energy source and affected by the proximate body tissue, a flexible sealed envelope in which said substrate is disposed and a signal conductor connected to said sensor and adapted for connection to said monitoring or measuring device.

14. A sensor appliance according to claim 13 further comprising a malleable spine disposed in said envelope.

15. A sensor appliance according to claim 14 wherein said malleable spine comprises a material opaque to said energy.

16. A sensor appliance according to claim 13 wherein said substrate is substantially U-shaped having an inner surface comprising said first surface, said energy radiating means and sensor means each being mounted on said inner surface in mutually facing relationship.

17. A sensor appliance according to claim 13 further comprising a flexible spacer disposed between said substrate and said envelope and having respective apertures in alignment with said energy source and said sensor for permitting transmission of said energy from said energy source through said cover, to the tissue and then through said envelope to said sensor.

* * * * *